United States Patent [19]

Wu et al.

[11] 4,308,409

[45] * Dec. 29, 1981

[54] PREPARATION OF PROPYLENE GLYCOL FROM PROPYLENE

[75] Inventors: Ching-Yong Wu, Fox Chapel Borough; Thaddeus P. Kobylinski, Gibsonia; John E. Bozik, Plum Borough, all of Pa.

[73] Assignee: Gulf Research & Development Company, Pittsburgh, Pa.

[*] Notice: The portion of the term of this patent subsequent to Mar. 10, 1998, has been disclaimed.

[21] Appl. No.: 172,859

[22] Filed: Jul. 28, 1980

Related U.S. Application Data

[63] Continuation-in-part of Ser. No. 948,241, Oct. 3, 1978, abandoned.

[51] Int. Cl.$^3$ ............................................... C07C 29/04
[52] U.S. Cl. .................................... 568/860; 568/311; 568/815
[58] Field of Search ......................................... 568/860

[56] References Cited

U.S. PATENT DOCUMENTS

| | | | |
|---|---|---|---|
| 2,575,403 | 11/1951 | Young et al. | 568/814 |
| 2,867,666 | 1/1959 | Erickson et al. | 568/815 |
| 3,351,635 | 11/1967 | Kollar | 568/815 |
| 3,526,674 | 9/1970 | Becker et al. | |
| 3,665,047 | 5/1972 | Gislon et al. | |
| 3,822,321 | 7/1974 | Maurin et al. | 568/860 |
| 3,860,662 | 1/1975 | Kollar | 568/815 |
| 4,049,724 | 9/1977 | Sheng et al. | 568/860 |
| 4,229,601 | 10/1980 | Wu et al. | 568/860 |
| 4,255,596 | 3/1981 | Wu et al. | 568/860 |

OTHER PUBLICATIONS

Sharpless et al., "J. Am. Chem. Soc.", 98:7 (Mar. 31, 1976), pp. 1986–1987.

*Primary Examiner*—Joseph E. Evans
*Attorney, Agent, or Firm*—Deane E. Keith; Forrest D. Stine; Donald L. Rose

[57] ABSTRACT

Propylene is converted to propylene glycol at high selectivity in a process in which ethylbenzene hydroperoxide and water are reacted with propylene in the presence of osmium tetroxide catalyst and a base at a pH of about 14.

8 Claims, No Drawings

PREPARATION OF PROPYLENE GLYCOL FROM PROPYLENE

This application is a continuation-in-part of U.S. Ser. No. 948,241, filed Oct. 3, 1978 now abandoned.

SUMMARY OF THE INVENTION

This invention relates to a procedure for reacting propylene with ethylbenzene hydroperoxide to produce propylene glycol at high selectivity.

We have discovered a process by which propylene can be converted to propylene glycol at excellent overall selectivity. In our procedure a reactor containing a solution of ethylbenzene hydroperoxide in ethylbenzene and an organic polar solvent together with a small amount of a tetraalkylammonium hydroxide and osmium tetroxide is pressured with propylene. The product mixture contains propylene glycol with no measureable amounts of undesired oxidation by-products being present in the product mixture.

DESCRIPTION OF THE INVENTION

Propylene glycol is currently produced commercially by several multistage processes from propylene. In these processes propylene is converted to propylene oxide. The propylene oxide is then hydrated either catalytically using a dilute aqueous solution of a strong acid or at high temperatures and pressures, with some dipropylene and tripropylene glycols being formed as by-products. No method for the direct production of propylene glycol has been commercially attractive.

U.S. Pat. No. 4,049,724 describes the direct preparation of propylene glycol from propylene in an aqueous system using osmium tetroxide and specifying stable and water-soluble aliphatic hydroperoxides such as tert-butyl hydroperoxide while a critical pH of 8 to 12 is maintained with a suitable combination of alkali metal buffering compounds. Ethylbenzene hydroperoxide, which is relatively unstable and is not water soluble or aliphatic, is not specified in the patent. The preparation of propylene glycol utilizing tert-butyl hydroperoxide is exemplified in the patent at a selectivity based on the hydroperoxide of 45 percent. When this reaction was attempted by us using ethylbenzene hydroperoxide in place of the tert-butyl hydroperoxide and a stoichiometric excess of propylene, a selectivity based on the hydroperoxide of only 2.3 percent to propylene glycol resulted.

Sharpless et al, JACS, 98:7, pages 1986-1987 reports the preparation of the diol of 1-decene at a yield of only 73 percent based on the 1-decene. The ketol of 1-decene is specified to be a major by-product of this reaction. The production of such ketols has been a persistent problem in efforts to convert olefins to diols. Sharpless et al utilize tert-butyl hydroperoxide in a tert-butyl alcohol solution containing tetraethylammonium hydroperoxide, water and osmium tetroxide catalyst. When this procedure was repeated by us using ethylbenzene hydroperoxide instead of tert-butyl hydroperoxide, the yield of the diol of 1-decene based on the 1-decene diminished to 24.8 percent with the selectivity based on the ethylbenzene hydroperoxide being a trivial 15.5 percent.

Notwithstanding this highly negative information regarding oxidations using ethylbenzene hydroperoxide, we have surprisingly discovered that ethylbenzene hydroperoxide and propylene readily react in a combined ethylbenzene solvent and organic polar solvent containing a tetraalkylammonium hydroxide and osmium tetroxide to form propylene glycol at an excellent selectivity based on propylene. Selectivities as high as 95 percent and higher can be obtained.

Ethylbenzene hydroperoxide is prepared as a solution in ethylbenzene by the air oxidation of ethylbenzene at a temperature between about 120° C. and about 150° C. A yield of up to about 25 percent ethylbenzene hydroperoxide can be obtained at a selectivity of about 80 to 95 percent depending on the reaction conditions. The primary by-products are acetophenone and 1-phenylethanol which are recovered together with the propylene glycol after the propylene hydroxylation reaction.

The reaction of ethylbenzene hydroperoxide with propylene is carried out in a homogeneous, single-phase reaction. When the relatively unstable ethylbenzene hydroperoxide is utilized in a heterogeneous, two-phase reaction, a substantial portion of the ethylbenzene hydroperoxide decomposes in the nonreacting phase. Therefore, we have determined that a homogeneous reaction system is essential for high selectivity. Since ethylbenzene hydroperoxide is not significantly soluble in water, a nonaqueous reaction medium must be used to obtain a homogeneous reaction system. Since the osmium tetroxide catalyst as well as ethylbenzene hydroperoxide and the tetraalkylammonium hydroxide are soluble in many organic polar solvents, a polar solvent is used in combination with the ethylbenzene solvent for this homogeneous reaction.

If the reaction of propylene with ethylbenzene hydroperoxide is carried out under anhydrous conditions, 1-phenylethanol, acetophenone and propylene glycol are produced in equimolar amounts according to the following equation:

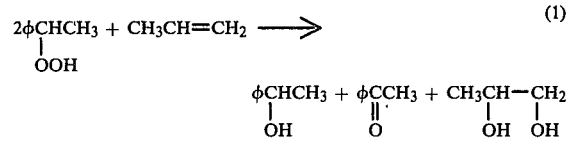

If water, which is slightly soluble in the solution is present in the reaction vessel, it will enter into the reaction according to the following equation:

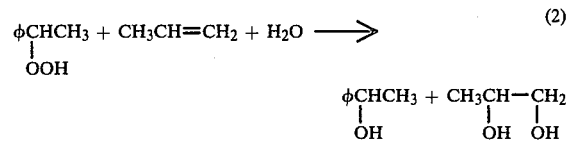

Since in actual practice both reactions take place with water present, the selectivity to propylene glycol based on ethylbenzene hydroperoxide can be adjusted to some extent by controlling the amount of water present in the reactor.

This reaction is carried out in the presence of a catalytic amount of osmium tetroxide using a polar solvent to ensure a homogeneous reaction since the osmium tetroxide is soluble in the polar solvent. Also present as a solvent is the unoxidized ethylbenzene which is introduced as the predominant component in the ethylbenzene hydroperoxide solution. The reaction solution is maintained strongly alkaline by the presence of a tetraalkylammonium hydroxide which is dissolved therein.

The polar solvent can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms, an aliphatic or aromatic sulfone having from two to about fourteen carbon atoms, and the like. Examples of suitable polar solvents include methanol, ethanol, propanol, butanol, hexanol, decanol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and the like. The amount of polar solvent can be between about 30 and about 98 weight percent of the reaction mixture, but will preferably comprise between about 50 and 80 percent of the reaction mixture.

The amount of ethylbenzene hydroperoxide used in the reaction is not critical but will generally be from about one percent to about 20 weight percent of the reaction system, preferably from about five percent to about 20 percent of the reaction mixture. The amount of ethylbenzene in the reaction system can vary between about 2.5 percent and about 50 weight percent but at preferred conditions of operation it will comprise between about ten and about 30 weight percent of the reaction mixture.

Since propylene is a gas, it is incorporated into the reaction solution either by condensing it into the reactor using a cooling bath or by charging it to the reactor as a liquefied gas. The pressure is not critical, rather it determines the amount of propylene that is present in the reaction solution. We find that a pressure between about 5 and about 150 psig. is useful, however, we prefer to operate within a pressure range of between about 10 and about 50 psig. The reaction is preferably carried out with a stoichiometric excess of propylene to substantially completely react all of the ethylbenzene hydroperoxide in the reaction mixture, and more preferably at least about a 25 percent stoichiometric excess of the propylene.

The osmium tetroxide is used in catalytic quantities. We find that from about 0.01 to about ten mmols of the catalyst per 100 ml. of the reaction solution is suitable, however, we prefer to carry out the reaction using from about 0.03 to about 0.1 mmol of catalyst per 100 ml. of the reaction solution. The amount of catalyst can also be related to the amount of osmium metal that is used. Thus, about 50 to about 1,000 ppm. osmium can be used based on the total reaction solution in the reaction vessel, preferably about 100 to about 500 ppm. osmium. Also included in the term osmium tetroxide as used herein including the claims are osmium compounds which are converted to osmium tetroxide by ethylbenzene hydroperoxide, such as potassium, sodium and lithium osmate, and the like.

A small amount of a tetraalkylammonium hydroxide is also present in the reaction solution, sufficient in amount to maintain the reaction solution at a pH of about 14. This tetraalkylammonium hydroxide serves in this reaction system as a base as well as a phase transfer agent and as such it increases the solubility of propylene in the reaction liquid. Therefore, the tetraalkylammonium hydroxide aided by its basic properties serves to increase the reaction rate, increase the selectivity to desired products and improve the overall efficiency of the reaction.

The useful tetraalkylammonium hydroxides include those containing lower alkyl groups having from one to about five carbon atoms such as tetramethylammonium hydroxide, tetrapropylammonium hydroxide, tetra-n-butylammonium hydroxide, and the like. This base is used in an amount between about 0.1 and about five weight percent of the reaction solution, but is is preferred to use it within the range of about 0.2 to about two weight percent of the reaction solution. Since these bases are conventionally supplied in aqueous solution, the water for reaction, if reaction under equation (2) is desired, can be supplied by this solution. This water of reaction is used in an amount up to about twenty weight percent of the reaction solution, but generally it is used in an amount between about one and about ten percent.

The hydroxylation reaction is carried out at a moderate temperature. At higher temperatures the reaction rate increases substantially but this occurs at a significant reduction in selectivity to propylene glycol. At very low temperatures the selectivity to propylene glycol is excellent but the reaction rate is slow. Within those general constraints we find that a reaction temperature between about $-10°$ C. to about 30° C. is particularly suitable but we prefer to operate within the range of about $-10°$ C. to about 25° C.

This hydroxylation reaction can be carried out as a batch reaction, as a continuous reaction or as a semi-continuous reaction. In the batch reaction all the necessary components are placed in a reaction vessel and the reaction is allowed to proceed for about one to about 24 hours for substantially complete reaction of the ethylbenzene hydroperoxide. In the continuous process the components can be introduced into the inlet of an elongated reactor at a rate that substantially complete reaction will have taken place by the time the reaction solution reaches the reactor outlet. The reaction can also be carried out in a semi-continuous manner by metering the reaction components into the first of one or more tank reactors in series while a stream of the reaction mixture is withdrawn at the same rate.

The reaction product, after removal of unreacted propylene, is a solution of product propylene glycol, 1-phenylethanol and acetophenone and also the polar solvent, ethylbenzene, tetraalkylammonium hydroxide, osmium tetroxide and water, if added. Since the reaction is generally carried out under conditions, including a stoichiometric excess of propylene, for complete reaction of the ethylbenzene hydroperoxide, there is no significant amount of hydroperoxide in the reaction product. If unreacted ethylbenzene hydroperoxide shows up in the reaction product, it is removed by the use of a suitable reducing agent in an extra processing step as a safety precaution to avoid possible hazards resulting from the undesired decomposition of the hydroperoxide during product work-up. Therefore, insuring the substantial absence of ethylbenzene hydroperoxide in the reaction product is a safety procedure and avoids extra processing costs.

The reaction product is characterized by the substantial absence of oxidation products other than propylene glycol. The volatile components are distilled out of the reaction mixture into various fractions leaving the osmium tetroxide in the still. Propylene glycol is separated from the high boiling distillate leaving a mixture of 1-phenylethanol and acetophenone from which the ethylbenzene can be regenerated by a suitable hydrogenation procedure.

DESCRIPTION OF PREFERRED EMBODIMENTS

In the following examples the ethylbenzene hydroperoxide was analyzed by iodometric titration. Propylene glycol analysis was carried out by gas chromatography and mass spectroscopic analysis.

EXAMPLE 1

Ethylbenzene hydroperoxide was reacted with propylene to produce a mixture of 1-phenylethanol, acetophenone and propylene glycol.

A charge of 100 ml. of t-butanol, 5 ml. of 0.5 percent osmium tetroxide (0.1 mmol) in t-butanol and 7.5 ml. of ten percent aqueous tetraethylammonium hydroxide was placed in a 300 ml. thick-walled glass reactor equipped with a thermocuple and a stirring magnet. The solution was cooled to 0° C. in an ice-salt bath. After adding 59 g. of 20 percent ethylbenzene hydroperoxide (80 mmols) to the chilled solution, the reactor was sealed. Propylene (10 g.) was introduced into the reactor from a charge tube. The pH of the solution was 14. The temperature inside the reactor rose to 13° C. and the pressure rose to about 80 psi. In about 20 minutes the reactor temperature returned to 0° C. and the reaction was allowed to proceed for six hours at 0° C. The reactor was then permitted to stand overnight at room temperature. After evaporating the product, 100 ml. of ethanol were added to precipitate the inorganic portion. Analysis of the evaporated filtrate showed 3.39 g. of propylene glycol (44.6 mmols) which represented a yield of 58 percent based on the ethylbenzene hydroperoxide and a selectivity of 95 percent based on reacted propylene. There was also a 98 percent selectivity of the ethylbenzene hydroperoxide to 1-phenylethanol and acetophenone.

EXAMPLE 2

In this experiment the reaction of 1-decene and tert-butyl hydroperoxide is carried out by the procedure described in the Sharpless et al report.

In a 500 ml. round bottom flask was placed 200 ml. tert-butyl alcohol, 15 ml. of 10 percent aqueous tetraethylammonium hydroxide (about 10 mmols) and 19 ml. (14 g., 100 mmols) 1-decene. The solution was cooled to <0° C. in an ice-salt bath with stirring. Then 23 ml. of 70 percent tert-butyl hydroperoxide were added (160 mmols), followed by 10 ml. of 0.5 percent osmium tetroxide in tert-butyl alcohol (about 0.2 mmol). The solution became purple in color. This was stirred for two hours at 0° C.

After refrigerating the flask at about 3° C., it was observed to have a pale yellow color. Thereupon, 100 ml. of 5 percent by weight NaHSO$_3$ in H$_2$O were added. The color became a murky purple which gradually became pale pink with stirring and warming to room temperature. The flask was then placed in a rotary evaporator and the tert-butyl alcohol and H$_2$O were removed. A pasty yellow jelly remained. This was taken up in 100 ml. of ether, in which it dissolved quite readily. The ether solution was transferred to a separatory funnel and washed with several 200 ml. portions of saturated brine solution. The final washing was made and the layers separated. The organic layer was dried with MgSO$_4$, filtered, and the ether evaporated on a rotary evaporator. There seemed to be some solid suspended, so the material was filtered, ether added, and the evaporation continued at 70° C. A 15.82 g. liquid product was obtained. Gas-liquid chromatographic analysis showed it to be 81.8 weight percent diol. This represents a 74.4 percent selectivity based on 1-decene and 46.5 percent selectivity based on tert-butyl hydroperoxide.

EXAMPLE 3

This experiment demonstrates that the process of Example 2 is not useful when ethylbenzene hydroperoxide replaces the tert-butyl hydroperoxide.

A 14 g. (100 mmols) sample of 1-decene, 200 ml. of t-butanol and 15 ml. of ten percent aqueous tetraethylammonium hydroxide were added to a 500 ml. round bottom flask. The flask and contents were cooled to 0° C. in a sodium chloride ice bath. After reaching temperature, 113 g. of 20 percent (160 mmols) ethylbenzene hydroperoxide and 10 ml. of 0.5 percent osmium tetroxide in t-butanol were added. The reaction was allowed to proceed for about 15 hours. Analysis after product recovery showed that the reaction with ethylbenzene hydroperoxide had formed 4.32 g. (24.8 mmols) of 1,2-dihydroxydecane, a 15.5 percent selectivity based on the ethylbenzene hydroperoxide. This also represents a 24.8 percent selectivity to the diol based on the 1-decene, which had completely reacted.

EXAMPLE 4

In this experiment the reaction of tert-butyl hydroperoxide and propylene in an aqueous, buffered system as described in Example III of Patent No. 4,049,724 is reviewed.

A 300 ml. thick-walled glass reactor equipped with a stirring magnet was charged with 18.5 g. of water, 1.0 g. Na$_2$CO$_3$, 1.2 g. NaHCO$_3$ and 0.2 mmol of osmium tetroxide. A measured 26 g. portion of propylene and 15 cc. of 70 percent tert-butyl hydroperoxide (98 mmols) were charged into the reactor. The reaction mixture was stirred at ambient temperature (20°–25° C.) for two hours. The reaction temperature rose from 25° C. to 45° C. and then slowly dropped back to 25° C. The stirring was continued for an additional 30 minutes to insure complete reaction of the hydroperoxide. Analysis of the reaction product disclosed the production of 1.7 g. (22.4 mmols) of propylene glycol which was a selectivity of 23 percent based on the tert-butyl hydroperoxide.

EXAMPLE 5

In this experiment it is demonstrated that the procedure including an aqueous, buffered reaction system as described in Example III of U.S. Pat. No. 4,049,724 is not useful for the preparation of a propylene glycol from ethylbenzene hydroperoxide and propylene.

The procedures and quantities of Example 4 were repeated except that 33 g of propylene were used and the tert-butyl hydroperoxide was replaced with 71.5 g. of 19 percent ethylbenzene hydroperoxide (98 mmols). The pH of the solution was 9.2. Analysis of the product disclosed that 0.17 g. of propylene glycol had been produced (2.24 mmols) which is a selectivity of 2.3 percent based on the ethylbenzene hydroperoxide.

It is to be understood that the above disclosure is by way of specific example and that numerous modifications and variations are available to those of ordinary skill in the art without departing from the true spirit and scope of the invention.

We claim:

1. A method of preparing propylene glycol in a homogeneous, single-phase reaction which comprises contacting ethylbenzene hydroperoxide with an excess of propylene at a pressure of between about 5 and about 150 psig. in a solution comprising between about 2.5 and about 50 weight percent ethylbenzene, between about one and about 20 weight percent ethylbenzene hydroperoxide and between about 30 and about 98 weight percent of an organic polar solvent in the presence of a sufficient amount of a tetraalkylammonium hydroxide in which the alkyl group has from one to about five carbon atoms to give a pH of about 14 and a catalytic amount of osmium tetroxide at a moderate temperature.

2. A method of preparing propylene glycol in accordance with claim 1 in which there is up to about twenty percent water.

3. A method of preparing propylene glycol in accordance with claim 2 in which the polar solvent is selected from aliphatic alcohols, aliphatic ketones and aliphatic ethers having up to about six carbon atoms.

4. A method of preparing propylene glycol in accordance with claim 2 in which there is about 100 to about 500 ppm. osmium as the metal based on the reaction solution.

5. A method of preparing propylene glycol in accordance with claim 2 in which there is about 0.1 to about five weight percent of the tetraalkylammonium hydroxide.

6. A method of preparing propylene glycol in accordance with claim 2 in which the temperature is between about $-10°$ C. and about 30° C.

7. A method of preparing propylene glycol in accordance with claim 1 in which there is at least about a 25 percent stoichiometric excess of propylene.

8. A method of preparing propylene glycol in accordance with claim 2 in which there is at least about a 25 percent stoichiometric excess of propylene.

* * * * *